US006774282B1

(12) United States Patent
Ritchie

(10) Patent No.: US 6,774,282 B1
(45) Date of Patent: Aug. 10, 2004

(54) MAIZE METALLOTHIONEIN GENE AND PROMOTER

(75) Inventor: Steven W. Ritchie, Granger, IA (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/520,268

(22) Filed: Mar. 7, 2000

Related U.S. Application Data

(60) Provisional application No. 60/123,510, filed on Mar. 8, 1999.

(51) Int. Cl.$^7$ .................... C12N 15/82; C12N 15/29; A01H 5/00; A01H 5/10
(52) U.S. Cl. ................ 800/287; 800/298; 800/320.1; 536/24.1; 435/320.1; 435/419
(58) Field of Search .................. 435/320.1, 419, 435/468; 536/24.1; 800/287, 298, 320.1

(56) References Cited

U.S. PATENT DOCUMENTS

| 5,466,785 A | 11/1995 | de Framond |
| 5,608,144 A | 3/1997 | Baden et al. |
| 5,785,735 A | 7/1998 | Raskin et al. |
| 5,837,848 A | 11/1998 | Ely et al. |
| 5,981,840 A | 11/1999 | Zhao et al. |

FOREIGN PATENT DOCUMENTS

| JP | 05192172 | 8/1993 |
| WO | WO 94/21793 | 9/1994 |
| WO | WO 97/38106 | 10/1997 |
| WO | WO 99/42587 | 8/1999 |
| WO | WO 99/43819 | 9/1999 |
| WO | WO 99/50427 | 10/1999 |
| WO | WO 00/15812 | 3/2000 |

OTHER PUBLICATIONS

Verdaguer et al, "Functional organization of the cassava vein mosaic virus (CsVMA) promoter", 1998, Plant Molecular Biology vol. 37, pp. 1055–1067.*
Chevalier, C. et al., Molecular Cloning and Characterization of Six cDNAs Expressed During Glucose Starvation in Excised Maize (*Zea mays* L.) Root Tips, Plant Molecular Biology (1995), pp 473–485, vol. 28.
De Framond, A., A Metallothionein–Like Gene From Maize (*Zea Mays*) Cloning and Characterization, Federation of European Biochemcial Societies, (1991), pp. 103–106, vol. 290: 1.2.
Evans, I., et al., A Gene From Pea (*Pisum sativum* L.) with Homology to Metallothionein Genes, Federation of European Biochemical Societies, (1990), pp. 29–32, vol. 262:1.
Hsieh, H., et al., Promoter Structure and Activity of Type I Rice Metallothionein–Like Gene, The Journal of Sequencing and Mapping, (1998), pp. 1–18, vol. 9:1.

Hsieh, H., et al., A Novel Stress–Inducible Metallothionein––Like Gene From Rice, Plant Molecular Biology, (1995), pp. 381–389, vol. 28.
Hudspeth, R., et al., Characterization and Expression of Metallothionein–Like Genes in Cotton, Plant Molecular Biology, (1996), pp. 701–705, vol. 31.
Newton, K., et al., Evidence for a Novel Mitochondrial Promoter Preceding the Cox2 Gene of Perennial Teosintes, (1995), pp. 585–593, vol. 14:3.
Capone, I., et al., Expression in Different Populations of Cells of the Root Meristem is Controlled by Different Domains of the rolB Promoter, Plant Molecular Biology, 1994, vol. 25, pp. 681–691.
Goddemeier, M.L., et al., Root–Specific Expression of a *Zea Mays* Gene Encoding a Novel Clycine–Rich Protein, zmGRP3, Plant Molecular Giology, 1998, vol. 36, pp. 799–802.
Hertig, C., et al., Sequence and Tissue–Specific Expression of a Putative Peroxidase Gene from Wheat (*Triticum Aestivum* L.), Plant Molecular Biology, 1991, vol. 16, pp. 171–174.
Li, H., et al., Novel Strategy Yields Candidate Gsh–I Homeobox Gene Targets Using Hypothalamus Progenitor Cell Lines, Developmental Biology, 1999, vol. 211, pp. 64–76.
Lipshutz, R.J., et al., High Density Synthetic Oligonucleotide Arrays, Nature America Inc., 1999, vol. 21, pp. 20–24.
Lohmer, S., et al., The Maize Regulatory Locus Opaque–2 encodes a DNA–Binding Protein Which Activates the Transcription of the B–32 Gene, The EMBO Journal, 1991, vol. 10, No. 3, pp. 617–624.
Luschnig, C., et al., ETR1; A Root–Specific Protein Involved in Auxin Transport, is Required for Gravitropism in *Arabidopsis thaliana*, Genes and Development, 1998, vol. 12, pp. 2175–2187.

(List continued on next page.)

Primary Examiner—David T. Fox
Assistant Examiner—Cynthia Collins
(74) Attorney, Agent, or Firm—Alston & Bird LLP

(57) ABSTRACT

The present invention provides compositions and methods for regulating expression of heterologous nucleotide sequences in a plant. Compositions include a novel nucleotide sequence for a root-preferred promoter for the gene encoding, a metallothionein gene and sequences isolated therefrom. A method for expressing a heterologous nucleotide sequence in a plant using the promoter sequences disclosed herein is provided. The method comprises transforming a plant cell with a nucleotide sequence operably linked to one of the root-preferred promoters of the present invention and regenerating a stably transformed plant that expresses the nucleotide sequence in a root-preferred manner from the transformed plant cell. Compositions and methods for expressing metallothionein genes in plants, plant cells and tissues are also provided. The compositions comprise nucleotide sequences encoding plant metallothionein. The sequences are useful in transforming plants for tissue-preferred or constitutive expression of metallothionein. Such sequences find use in modulating levels of metal ions in plants and plant tissues.

11 Claims, 3 Drawing Sheets

OTHER PUBLICATIONS

Masuda, S., et al., cDNA Cloning of a Novel Lectin–Like Xylem Sap Protein and Its Root–Specific Expression in Cucumber, Plant Cell Physiol.,1999, vol. 40, No. 11, pp. 1177–1181.

Robinson, N.J., et al., Plant Metallothioneins, Biochem. J., 1993, vol. 295, pp. 1–10.

Takahashi, Y., et al., Characterization of the Auxin–Regulated Par Gene From Tobacco Mesophyll Protoplasts, The Plant Journal, 1991, vol. 1, No. 3, pp. 327–332.

Takahashi, Y., et al., Location of the Cis–Acting Auxin–Responsive Region in the Promoter of the Par Gene From Tobacco Mesophyll Protoplasts, Proc. Natl. Acad. Sci., 1990, vol. 87, pp. 8013–8016.

Xu, Y., et al., Characterization of a Rice Gene Family Encoding Root–Specific Proteins, Plant Moleuclar Biology, 1995, vol. 27, pp. 237–248.

Yamamoto, Y.T., et al., Characterization of CIS–Acting Sequences Regulating Root–Specific Gene Expression in Tobacco, The Plant Cell, 1991, vol. 3, pp. 371–382.

* cited by examiner

Tissue Distribution of Two Metallothionein Groups

MAIZE METALLOTHIONEIN GENE AND PROMOTER

CROSS-REFERENCE TO RELATED APPLICATIONS

This application claims the benefit of U.S. Provisional Application No. 60/123,510, filed Mar. 8, 1999.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Thus far, the regulation of gene expression in plant roots has not been adequately studied despite the root's importance to plant development. To some degree this is attributable to a lack of readily available, root-specific biochemical functions whose genes may be cloned, studied, and manipulated. Genetically altering plants through the use of genetic engineering techniques and thus producing a plant with useful traits requires the availability of a variety of promoters. An accumulation of promoters would enable the investigator to design recombinant DNA molecules that are capable of being expressed at desired levels and cellular locales. Therefore, a collection of tissue-preferred promoters would allow for a new trait to be expressed in the desired tissue. Several genes have been described by Takahashi et al. (1991), *Plant J*. 1:327–332; Takahashi et al. (1990), *Proc. Natl. Acad. Sci. USA* 87:8013–8016; Hertig et al. (1991), *Plant Mol Biol*. 16:171–174; Xu et al. (1995), *Plant Mol Biol*. 27:237–248; Capone et al. (1994), *Plant Mol Biol*. 25:681–691; Masuda et al. (1999), *Plant Cell Physiol*. 40(11):1177–81; Luschnig et al. (1998), *Genes Dev*. 12(14): 2175–87; Goddemeier et al. (1998), *Plant Mol Biol*. 36(5): 799–802; and Yamamoto et al. (1991), *Plant Cell*. 3(4): 371–82 to express preferentially in plant root tissues.

Metallothioneins (MT's) are proteins or polypeptides that bind and sequester ionic forms of certain metals in plant and animal tissues. Examples of such metals include copper, zinc, cadmium, mercury, gold, silver, cobalt, nickel and bismuth. The specific metals sequestered by MT's vary for the structurally distinct proteins/polypeptides occurring in different organisms. Plants appear to contain a diversity of metal-binding MT's with the potential to perform distinct roles in the metabolism of different metal ions. In plants, MT's are suggested to have roles in metal accumulation, metal intoxication, and embryogenesis.

Typically, MT's and MT-like proteins are Cys-rich proteins, characterized by the presence of Cys-Xaa-Cys motifs suggesting the capability of binding metal ions. Further categories of MT-like proteins have been proposed on the basis of the predicted locations of Cys residues and designated types 1 and 2. In type 1 there are exclusively Cys-Xaa-Cys motifs, whereas in type 2 there is a Cys-Cys and a Cys-Xaa-Xaa-Cys pair within the N-terminal domain. The type 1 motif has been implicated in the binding and sequestration of copper.

Several metallothionein-like plant genes have been isolated, including those from pea, maize, barley, mimulus, soybean, castorbean and arabidopsis. See Robinson et al. (1993) *Biochem J*. 295: 1–10. Sequences expressed in roots have been reported to be isolated from pea, as described in Evans et al. (1990) *FEBS Lett* 262:29–32. A maize root MT gene has been described in U.S. Pat. No. 5,466,785; though this sequence is also expressed leaves, pith and seed, as described in de Framond (1991) *FEBS Lett* 290:103–106.

Thus, isolation and characterization of tissue-preferred, particularly root-preferred, promoters that can serve as regulatory regions for expression of heterologous nucleotide sequences of interest in a tissue-preferred manner are needed for genetic manipulation of plants. Furthermore, isolation and characterization of sequences involved in metal-binding and accumulation are needed for influencing metabolism of metals in plants.

SUMMARY OF THE INVENTION

Compositions and methods for regulating expression of heterologous nucleotide sequences in a plant are provided. Compositions comprise novel nucleotide sequences for promoters that initiate transcription in a root-preferred manner. More particularly, a transcriptional initiation region isolated from a plant metallothionein gene, is provided. A method for expressing a heterologous nucleotide sequence in a plant using the transcriptional initiation sequences disclosed herein is provided. The method comprises transforming a plant cell with a transformation vector that comprises a heterologous nucleotide sequence operably linked to one of the plant promoters of the present invention and regenerating a stably transformed plant from the transformed plant cell. In this manner, the promoter sequences are useful for controlling the expression of operably linked coding sequences in a root-preferred manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel; function or product in the plant.

Also provided are compositions and methods for expressing metallothionein genes in plants, plant cells, and plant tissues. The compositions comprise nucleotide sequences for the expressed region of the MT gene, which comprise the nucleotide sequences encoding the metallothionein polypeptide. These sequences are useful in transforming plants for tissue-preferred or constitutive expression of metallothionein. Such sequences find use in modulating levels of metal ions in plants and plant tissues.

Expression cassettes comprising the sequences of the invention are provided. Additionally provided are transformed plant cells, plant tissues, and plants.

DETAILED DESCRIPTION OF THE INVENTION

Figure 1:
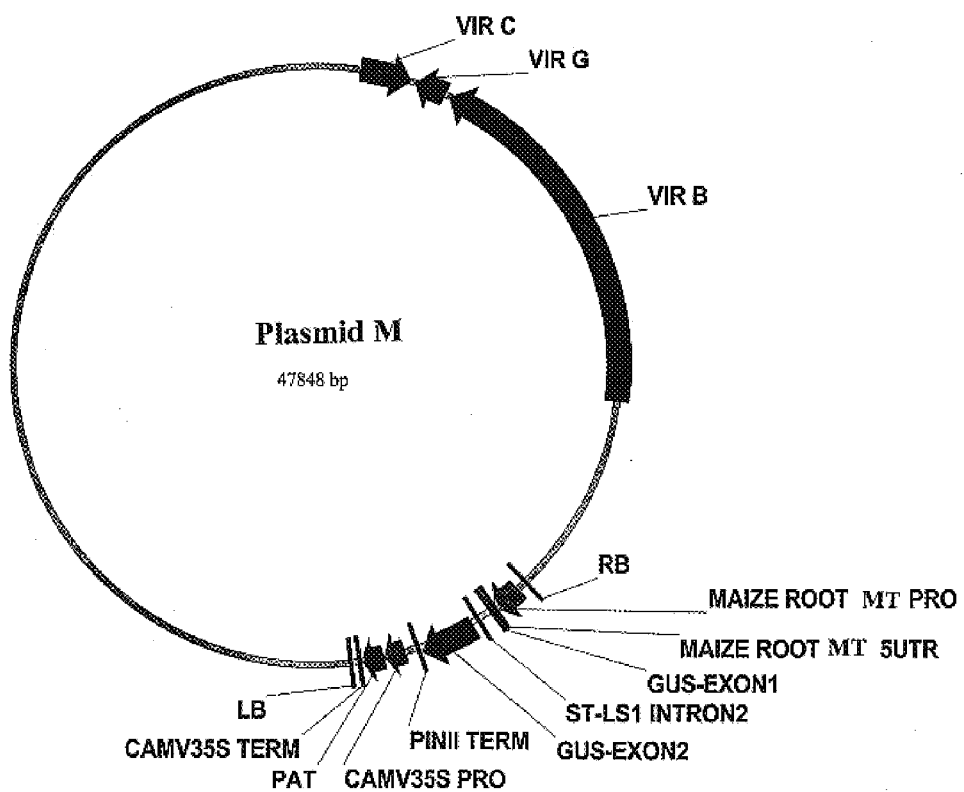
FIG. 1 depicts a construct used for Agrobacterium-mediated transformation utilizing an MT promoter of the invention.

The invention relates to compositions and methods drawn to plant metallothionein(MT) genes and methods of their use. The compositions comprise nucleotide sequences for the promoter region of the MT gene of the invention, as well as the nucleotide sequences for the expressed regions of the gene.

The MT promoter sequences of the present invention include nucleotide constructs that allow initiation of transcription in a tissue-preferred, more particularly in a root-preferred manner. Such constructs of the invention comprise regulated transcription initiation regions associated with plant developmental regulation. Thus, the compositions of the present invention comprise novel plant promoter nucleotide sequences, particularly root-preferred promoter sequences for the MT gene, more particularly a maize MT promoter sequence. The sequence for the maize MT promoter region is set forth in SEQ ID NO:1.

Also provided are compositions and methods for expressing MT genes in plants, plant cells, and specific plant tissues. Such compositions are nucleic acids and proteins relating to MT or MT-like genes in plants. More particularly, nucleotide sequences encoding maize MT and the amino acid sequences for the proteins encoded thereby are disclosed. The MT gene encodes a protein involved in binding and sequestering metal ions. The MT protein contains known Cys-rich motifs. The maize MT gene is abundantly expressed in maize root tissue. Nucleotide sequences for the expressed region of the maize MT gene comprising the MT coding sequences are set forth in SEQ ID NO:2. The maize MT polypeptide sequence is set forth in SEQ ID NO:3.

Compositions of the invention include the nucleotide sequences for the native MT promoter and expressed regions, the MT amino acid sequences, as well as fragments and variants thereof. The nucleotide sequences for the expressed region of the MT gene or corresponding antisense sequences find use in modulating the expression of metallothionein in a plant or plant cell. That is, the coding sequences are used to increase the expression while antisense sequences are used to decrease expression. The promoter sequences of the invention are useful for expressing sequences in a tissue-preferred, particularly a root-preferred manner. The sequences of the invention also find use in the construction of expression vectors for subsequent transformation into plants of interest, as probes for the isolation of other MT-like genes, as molecular markers, and the like.

In particular, the present invention provides for isolated nucleic acid molecules comprising the nucleotide sequences set forth in SEQ ID NOs:1 and 2, isolated nucleic acid molecules comprising nucleotide sequences encoding the amino acid sequences shown in SEQ ID NO:3, or the nucleotide sequences encoding the DNA sequences deposited in a bacterial host as Patent Deposit Nos. 207085 and 207086. Further provided are polypeptides having an amino acid sequence encoded by a nucleic acid molecule described herein, for example those set forth in SEQ ID NO:2, those deposited as Patent Deposit NO. 207086, and fragments and variants thereof.

Plasmids containing the nucleotide sequences of the invention were deposited with the Patent Depository of the American Type Culture Collection (ATCC), Manassas, Va., on Feb. 2, 1999 and assigned Patent Deposit NOs. 207085 and 207086. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals. The MT promoter sequences of the invention may be isolated from the 5' untranslated region flanking their respective transcription initiation sites. Methods for isolation of promoter regions are well known in the art.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a MT coding sequence may encode protein fragments that retain the biological activity of the native protein and hence bind metal ion. Fragments of a MT promoter sequence may retain the biological activity of driving root-preferred expression. Alternatively, fragments of a nucleotide sequence that are useful as hybridization probes generally do not encode fragment proteins or promoters retaining biological activity. Thus, fragments of a nucleotide sequence for the expressed region of the MT gene may range from at least about 27 nucleotides, about 50 nucleotides, about 100 nucleotides, and up to the full-length nucleotide sequence of the invention for the expressed region of the gene. Fragments of a nucleotide sequence for the promoter region of the MT gene may range from at least about 20 nucleotides, about 50 nucleotides, about 100 nucleotides, and up to the full-length nucleotide sequence of the invention for the promoter region of the gene.

A fragment of a MT nucleotide sequence that encodes a biologically active portion of a protein of the invention will encode at least 15, 25, 30, 50 contiguous amino acids, or up to the total number of amino acids present in a full-length MT protein of the invention (for example, 79 amino acids for SEQ ID NO:3). Fragments of a MT nucleotide sequence that are useful as hybridization probes or PCR primers generally need not encode a biologically active portion of a MT protein.

Thus, a fragment of a MT nucleotide sequence may encode a biologically active portion of a MT protein, MT promoter, or it may be a fragment that can be used as a hybridization probe or PCR primer using methods disclosed below. A biologically active portion of a MT protein can be prepared by isolating a portion of the nucleotide sequences of the invention for the expressed region of the MT gene, expressing the encoded portion of the protein (e.g., by recombinant expression in vitro), and assessing the activity of the encoded portion of the MT protein. Nucleic acid molecules that are fragments of a nucleotide sequence for the expressed region of the MT gene comprise at least 27, 50, 75, 100, 150, 200, 250, 300, 350, 400, 450, 500, 550, 600 or up to the number of nucleotides present in a full-length MT sequence disclosed herein (for example, 612 nucleotides for SEQ ID NO:2.

A biologically active portion of a MT promoter can be prepared by isolating a portion of the MT promoter sequence of the invention, and assessing the promoter activity of the portion. Nucleic acid molecules that are fragments of a MT promoter nucleotide sequence comprise at least about 16, 50, 75, 100, 150, 200, 250, 300, 350, 400, 450, 500, 550, 600, 650, 700 nucleotides, or up to the number of nucleotides present in a full-length MT promoter sequence disclosed herein (for example, 747 nucleotides for SEQ ID NO:1).

By "variants" is intended substantially similar sequences. For nucleotide sequences, naturally occurring variants can be identified with the use of well-known molecular biology techniques, as, for example, with polymerase chain reaction (PCR) and hybridization techniques as outlined below. For MT coding sequences, conservative variants include those sequences that, because of the degeneracy of the genetic code, encode the amino acid sequence of one of the MT polypeptides of the invention. Thus, for MT coding sequences, variants include naturally occurring allelic variants. Variant nucleotide sequences also include synthetically derived nucleotide sequences, such as those generated, for example, by using site-directed mutagenesis. For MT coding sequences, such synthetically derived sequences still encode a MT protein of the invention.

Generally, variants of a particular nucleotide sequence of the present invention will have at least 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, metal ion binding activity as described herein. Such variants may result from, for example, genetic polymorphism or from human manipulation. Biologically active variants of a native MT protein of the invention will have at least at least 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the MT proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired metal binding activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assessing metal ion binding to the isolated protein, or by assessing accumulation of metal ions in cells expressing the protein. See, for example, Robinson et al. (1993) *Biochem J.* 295: 1–10., herein incorporated by reference.

Variant nucleotide sequences and proteins also encompass sequences and proteins derived from a mutagenic and recombinogenic procedure such as DNA shuffling. With such a procedure, one or more different MT nucleotide sequences for the promoter or the expressed region of the gene can be manipulated to create a new MT promoter or protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the gene of the invention and other known MT genes to obtain a new gene coding for a protein with an improved property of interest, such as an increased affinity for metal ions. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire MT sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the MT sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire MT promoter sequence disclosed herein, or one or more portions thereof, may be used as a probe capable of specifically hybridizing to corresponding MT sequences and messenger RNAs. To achieve specific hybridization under a variety of conditions, such probes include sequences that are unique among MT sequences and are preferably at least about 10 nucleotides in length, and most preferably at least about 20 nucleotides in length. Such probes may be used to amplify corresponding MT sequences from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284 $T_m$=81.5° C. +16.6 (log M)+0.41 (%GC)–0.61 (% form)–50/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences with the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology— Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have root-preferred promoter activity or encode for a MT protein and which hybridize under stringent conditions to the MT sequences disclosed herein, or to fragments thereof, are encompassed by the present invention. Such sequences will be at least 70% homologous, and even about 75%, 80%, 85%, 90%, 95% to 98% homologous or more with the disclosed sequences. That is, the sequence identity of sequences may range, sharing at least 70%, and even about 75%, 80%, 85%, 90%, 95% to 98% or more sequence identity.

The following terms are used to describe the sequence relationships between two or more nucleic acids or polynucleotides(a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to, a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff(1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (Cofea spp.), coconut (*Cocos* nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), macadamia (Macadamia integrifolia), almond (Prunus amygdalus), sugar beets (Beta vulgaris), sugarcane (Saccharum spp.), oats, barley, vegetables, ornamentals, and conifers.

Heterologous coding sequences expressed by the promoters of the invention may be used for varying the phenotype of a plant. Various changes in phenotype are of interest including modifying expression of a gene in a plant root, altering a plant's pathogen or insect defense mechanism, increasing the plants tolerance to herbicides in a plant, altering root development to respond to environmental stress, and the like. These results can be achieved by providing expression of heterologous or increased expression of endogenous products in plants.

Alternatively, the results can be achieved by providing for a reduction of expression of one or more endogenous products, particularly enzymes, transporters, or cofactors, or affecting nutrient uptake in the plant. These changes result in a change in phenotype of the transformed plant.

General categories of genes of interest for the present invention include, for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, and herbicide resistance. It is recognized that any gene of interest can be operably linked to the promoter of the invention and expressed in plant roots.

Insect resistance genes may encode resistance to pests that have great yield drag such as rootworm, cutworm, European Corn Borer, and the like. Such genes include, for example, Bacillus thuringiensis toxic protein genes (U.S. Pat. Nos. 5,366,892; 5,747,450; 5,736,514; 5,723,756; 5,593,881; and Geiser et al. (1986) Gene 48:109); lectins (Van Damme et al. (1994) Plant Mol. Biol. 24:825); and the like.

Genes encoding disease resistance traits include detoxification genes, such as against fumonosin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as dehydration resulting from heat and salinity, toxic metal or trace-elements, or the like.

As noted, the heterologous nucleotide sequence operably linked to the MT promoters disclosed herein may be an antisense sequence for a targeted gene. Thus the promoter sequences disclosed herein may be operably linked to antisense DNA sequences to reduce or inhibit expression of a native protein in the plant root.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, translational fusions may be provided. Such fusions include portions of the amino acid sequence. Thus the promoter regions disclosed herein are generally further defined by comprising upstream regulatory elements such as, those responsible for tissue and temporal expression of the coding sequence, enhancers and the like. In the same manner, the promoter elements, which enable expression in the desired tissue such as the root, can be identified isolated and used with other core promoters to confer root-preferred expression. In this aspect of the invention, by "core promoter" is intended a promoter without promoter elements.

The compositions of the invention include promoter elements identified in the MT promoter sequences of the invention. These elements include, but are not limited to the promoter elements having the nucleotide sequences TAT-GAGATGA (SEQ ID NO:10); CGATCGACAA (SEQ ID NO:11); GGCACAAGA (SEQ ID NO:12); GATATAGAT (SEQ ID NO:13); AAATTAGCAGAGGA (SEQ ID NO:9); AGAGCACGC (SEQ ID NO:14); AGTTCTG (SEQ ID NO:15); AGCTGTA (SEQ ID NO:16); AT AGATTAC (SEQ ID NO:17). These elements correspond to nucleotides 39–48, 179–188, 295–303, 305–313, 422–436, 444–452, 520–526, 616–622, and 671–679 of the promoter sequence set forth in SEQ ID NO:1, respectively. It is determined that these elements contribute to the root-preferred expression of MT.

It is further determined that, these promoter elements, when introduce into minimal or constitutive promoters, direct root preferred expression in a plant the invention encompasses promoters that drive root-preferred expression and comprise at least one copy of at least one root-preferred promoter element selected from the group consisting of TATGAGATGA (SEQ ID NO:10); CGATCGACAA (SEQ ID NO:11); GGCACAAGA (SEQ ID NO:12); GATATA-GAT (SEQ ID NO:13); AAATTAGCAGAGGA (SEQ ID NO:9); AGAGCACGC (SEQ ID NO:14); AGT TCTG (SEQ ID NO:15); AGCTGTA (SEQ ID NO:16); AT AGATTAC (SEQ ID NO:17).

In a preferred embodiment, the root-preferred promoter of the present invention comprises at least one copy of at least one promoter element selected among promoter elements having the nucleotide sequence CGATCGACAA (SEQ ID NO:11); AAATTAGCAGAGGA (SEQ ID NO:9); AGAG-CACGC (SEQ ID NO:14); AGTTCTG (SEQ ID NO:15); AGCTGTA (SEQ ID NO:16); ATAGATTAC (SEQ ID NO:17). In a more preferred embodiment, the root-preferred promoter of the present invention comprises at least one copy of the promoter element having the nucleotide sequence AGAGCACGC (SEQ ID NO:14).

The regulatory sequences of the present invention, when operably linked to a heterologous nucleotide sequence of interest and inserted into a transformation vector, drive root-preferred expression of the heterologous nucleotide sequence in the root stably transformed with this vector. By "root-preferred" is intended that expression of the heterologous nucleotide sequence is most abundant in the root including at least one of root cap, apical meristem, protoderm, ground meristem, procambium, endodermis, cortex, vascular cortex, epidermis, and the like. While some level of expression of the heterologous nucleotide sequence may occur in other plant tissue types, expression occurs most abundantly in the root including primary, lateral and adventitious roots.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host.

The isolated promoter sequences of the present invention can be modified to provide for a range of expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Generally, at least about 20 nucleotides of an isolated promoter sequence will be used to drive expression of a nucleotide sequence.

It is recognized that to increase transcription levels enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the invention may be used with their native MT coding sequences to increase or decrease expression, thereby resulting in a change in phenotype of the transformed plant. This phenotypic change could further effect an increase or decrease in levels of metal ions in tissues of the transformed plant.

The MT coding sequences of the present invention can be used with promoters known in the art. Such sequences find use in modulating uptake of metal ions. Such metals include cadmium, zinc, copper, mercury, gold, silver, cobalt, nickel, bismuth, and the like.

The MT coding sequences may additionally be used to regulate gene expression, particularly by coordination of zinc binding and expression during development. The MT proteins are implicated in the sequestration of copper in roots and play a role in metabolism of metal ions. Additionally, the MT polypeptides may play an antioxidant role as DNA strand-breakage, induced by oxidative stress, is reduced in the presence of elevated metallothionein levels. Thus, antisense constructs corresponding to MT coding sequences or MT antibodies may find use in increasing strand breakage for enhancement of transformation insertion events.

It is recognized that with the MT coding sequences, antisense constructions, complementary to at least a portion of the messenger RNA (mRNA) for the MT sequences can be constructed. It is also recognized that with the MT promoter sequences, antisense constructions, complementary to at least a portion of the messenger RNA (mRNA) for any targeted sequence(s) can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence;of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The coding sequences of the invention are useful for transforming plants and modulating levels of metal ions in a plant. By "modulating levels of metal ions" is intended an increase or a decrease in the amount of the ionic form of a metal. In this aspect of the invention, it is envisioned that the binding of the MT protein expressed by the sequences of the invention to a metal ion of interest will render a metal-ligand protein(MT) complex, thereby decreasing the amount of the ionic form of the metal. Alternatively, antisense sequences to the coding sequences of the invention may be used to increase the level of metal ions of interest. The metal ions are cations, more particularly divalent cations, even more particularly $Cu^{++}$.

Generally, decreased metal ion content in plant tissue may reduce the toxicity associated with excessive amounts of metal ions in the tissue. Toward this end, the sequences of the invention may be utilized in expression cassettes or DNA constructs with tissue-preferred promoters including but not limited to seed-specific promoters (those promoters active during seed development), as well as seed-germinating promoters (those promoters active during seed germination). Such seed-specific promoters include Cim1 (cytokinin-induced message); cZ19B1 (maize 19 KDa zein); mi1 ps (myo-inositol-1-phosphate synthase); celA (cellulose synthase); end 1 (*Hordeum verlgase* mRNA clone END1); alpha amylase; and imp3 (myo-inositol monophosphate-3). For dicots, particular promoters include phaseolin, napin, β-conglycinin, soybean lectin, and the like. For monocots, particular promoters include maize 15 Kd zein, 22 KD zein, 27 kD zein, waxy, shrunken 1, shrunken 2, globulin 1, etc.

For expression of the nucleotide sequences of the invention comprising the MT coding sequences, constitutive or tissue-preferred promoters may be utilized. Constitutive promoters would provide a constant supply of MT protein throughout the plant. Such constitutive promoters include, for example, the core promoter of the Rsyn 7 (copending U.S. patent application Ser. No. 08/661,601), the core CaMV35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The utilization of tissue-preferred promoters with the coding sequences of the invention would increase or decrease the availability of a metal ion of interest in specific tissues of the plant. For example, leaf-specific promoters may be utilized. Such tissue-preferred promoters include, Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. 1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci. USA* 90(20):9586–9590; and Guevara-Garcia et al. (1993) *Plant J.* 4(3):495–505.

In particular, one tissue-preferred promoter of interest includes root-preferred promoters. The utilization of such promoters would provide a mechanism for modulating the level of metal ions in the root, and influence the uptake of the metal ions by the root. Thus, the invention encompasses increasing root uptake of metal ions by expression of the coding sequences of the invention; and decreasing root uptake of metal ions by transforming roots with corresponding antisense sequences. Root-preferred promoters include the VfENOD-GRP3 gene promoter (Kuster H et al. (1995) *Plant Mol. Biol.* 29(4):759–772); and rolB promoter (Capana et al. (1994) *Plant Mol. Biol.* 25(4):681–691. See also U.S. Pat. Nos. 5,633,363; 5,459,252; 5,401,836; 5,110, 732; and 5,023,179 and the MT promoter sequences disclosed herein.

The nucleotide sequences disclosed in the present invention, as well as variants and fragments thereof, are useful in the genetic manipulation of any plant. The MT promoter sequences are useful in this aspect when operably linked with a heterologous nucleotide sequence whose expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention may be provided in expression cassettes along with heterologous nucleotide sequences of interest for expression in the plant of interest, more particularly in the root of the plant.

Such expression cassettes will comprise a transcriptional initiation region comprising one of the promoter nucleotide sequences of the present invention, or variants or fragments thereof, operably linked to the heterologous nucleotide sequence whose expression is to be controlled by the root-preferred promoters disclosed herein. Such an expression cassette is provided with a plurality of restriction sites for insertion of the nucleotide sequence to be under the transcriptional regulation of the regulatory regions. The expression cassette may additionally contain selectable marker genes.

The MT coding sequences of the invention are also provided in expression cassettes for expression in the plant of interest. The cassette will include 5' and 3' regulatory sequences operably linked to the sequence of interest.

The sequences of the invention can be introduced into any plant. The sequences to be introduced may be used in expression cassettes for expression in any plant of interest where expression in the plant is necessary for transcription. Plants of interest include, but are not limited to corn (*Zea mays*), canola (*Brassica napus, Brassica rapa* ssp.), alfalfa (*Medicago sativa*), rice (*Oryza saliva*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably plants include corn, soybean, sunflower, safflower, Brassica, wheat, barley, rye, alfalfa, and sorghum The expression cassette comprising the sequences of the invention will include in the 5'-to-3' direction of transcription, a transcriptional and translational initiation region, a nucleotide sequence of interest, and a; transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi heterologous et al. (1987) *Nucleic Acid Res.* 15:9627–9639.

The expression cassette comprising the sequences of the present invention may also contain at least one additional nucleotide sequence for a gene to be cotransformed into the organism. Alternatively, the additional sequence(s) can be provided on another expression cassette.

Where appropriate, the nucleotide sequences whose expression is to be under the control of the root-preferred promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (β-glucuronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):81 15 and Luehrsen et al. (1992) *Methods Enzymol.* 216:397–414) and the maize genes encoding for anthocyanin production (Ludwig et al. (1990) *Science* 247:449).

The expression cassette comprising the MT promoter or coding sequence of the present invention can be used to transform any plant. In this manner, genetically modified plants, plant cells, plant tissue, seed, root, and the like can be obtained.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27-37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et a 1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in

*The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The following examples are offered by way of illustration and not by way of limitation.

EXPERIMENTAL

The maize MT gene was isolated from maize plants. The nucleotide sequences for the maize MT promoter region is set forth in SEQ ID NO:1, and the nucleotide sequence for the expressed region of the gene is set forth in SEQ ID NO:2. The sequence for the expressed region of the MT gene set forth in SEQ ID NO:2 consists of the 5' untranslated region (5' UTR, nucleotides 1–68), the maize MT polypeptide encoding region (nucleotides 69–308), and the 3' untranslated region (ncleotides 309–612).

EXAMPLE 1

Isolation of MT Promoter Sequences

The procedure for promoter isolation is described in the User Manual for the Genome Walker kit sold by Clontech Laboratories, Inc., Palo Alto, Calif. Genomic DNA from maize line V3–4 A63 was prepared by grinding 10-day-old seedling leaves in liquid nitrogen, and the DNA prepared as described by Chen and Dellaporta (1994) in *The Maize Handbook*, ed. Freeling and Walbot (Springer-Verlag, Berlin) with a few minor modifications. Precipitated DNA was recovered using an inoculation loop and transferred to a 1.5 ml eppendorf tube containing 500 μl of TE(10 mM Tris pH 8.0, 1 mM EDTA). The DNA was allowed to dissolve at room temperature for 15 minutes, phenol extracted and 2-propanol precipitated in 700 μl. The precipitate was recovered and washed with 70% ethanol. The DNA was then placed in a clean 1.5 ml eppendorf tube to air dry and resuspended in 200 μl of TE. RNase A was added to 10 μg/ml and the mixture was incubated at 37° C. for several hours. The DNA was then extracted once with phenol-chloroform, then chloroform, then ethanol precipitated and resuspended in TE. The DNA was then used as described in the *Genome Walker User Manual* (Clontech PT3042-1 version PR68687). Briefly, the DNA was digested separately with restriction enzymes DraI, EcoRV, PvuII, ScaI, and StuI, all blunt-end cutters. The DNA was extracted with phenol, then chloroform, then ethanol precipitated. The Genome Walker adapters were ligated onto the ends of the restricted DNA. The resulting DNA is referred to as DL1-DL5, respectively.

For isolation of specific promoter regions, three nonoverlapping gene-specific primers (21–26 bp in length) were designed from the 5' end of the maize genes identified from sequence databases. The primers were designed to amplify the region upstream of the coding sequence, i.e. the 5' untranslated region and promoter of the chosen gene. The sequence of the primers are given below. The first round of PCR was performed on each DNA sample (DL–5) with Clontech primer AP1 (sequence 5' -gtaatacgactcactatagggc-3') and the gene-specific primer (gsp)1 with the sequences shown in SEQ ID NO:4.

PCR was performed in a model PTC-100 thermal cycler with HotBonnet from MJ Research (Watertown, Mass.) using reagents supplied with the Genome Walker kit and the Advantage Genomic PCR Kit (Clontech K1906-y). The following cycle parameters were used: 7 cycles of 94° C. for 2 seconds, then 72° C. for 3 minutes, followed by 37 cycles of 94° C. for 2 seconds and 67° C. for 3 minutes. Finally, the samples were held at 67° C. for 4 minutes and then at 4° C. until further analysis.

As described in the User Manual, the DNA from the first round of PCR was then diluted and used as a template in a second round of PCR using the Clontech AP2 primer (sequence 5 '-actatagggcacgcgtggt-3) (SEQ ID NO:18) and gene-specific primer (gsp)2 with the sequences shown in SEQ ID NO:5. The cycle parameters for the second round were 5 cycles of 94° C. for 2 seconds, then 72° C. for 3 minutes, followed by 20 more cycles of 94° C. for 2 seconds, then 67° C. for 3 minutes. Finally, the samples were held 67° C. for 4 minutes and then held at 4° C.

The DNA from the second round of PCR was then diluted and used as a template in a third round of PCR using the Clontech AP2 primer and gene-specific primer (gsp)3 with the sequence shown in SEQ ID NO:6. The cycle parameters for the third round of PCR were 93° C. for 1.5 minutes, followed by 35 cycles of 93° C. for 30 seconds, then 58° C. for 30 seconds, then 72° C. for 3 minutes Finally, the samples were held at 72° C. for 10 minutes and then held at 4° C. Approximately 10 μl of each reaction were run on a 0.7% agarose gel, transferred to a solid support and hybridized with a labeled probe designated CRVAC 17. Bands that bound to the CRVAC 17 probe (usually 500 bp or larger) were excised out of a separate 0.7% agarose gel, purified with the PCR Cleanup Kit (Promega, Madison, Wis.) and cloned into the Zero Blunt vector, pCR-Blunt (Invitrogen, San Diego, Calif.). Clones were sequenced for verification.

A clone designated rmp5B corresponding to the promoter sequence set forth in SEQ ID NO:1 upstream of nucleotides 1–65 of SEQ ID NO:2 was deposited as ATCC Patent Deposit NO:207085, and a cDNA corresponding to SEQ ID NO:2 and the CRVAC17 probe was deposited as ATCC deposit NO: 207086; as indicated above.

EXAMPLE 2

Transformation and Regeneration of Transgenic Plants

Immature maize embryos from greenhouse donor plants are bombarded with a plasmid containing a gene of interest operably linked to a MT promoter of the invention, or a plasmid comprising the MT coding sequences of the invention operably linked to a desired promoter (e.g. a ubiquitin promoter), plus a plasmid containing the selectable marker gene PAT (Wohlleben et al. (1988) *Gene* 70:25–37) that confers resistance to the herbicide Bialaphos. Transformation is performed as follows. Media recipes follow below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a gene of interest operably linked to a MT promoter of the invention, or a plasmid comprising the MT coding sequences of the invention operably linked to a desired promoter (e.g. a ubiquitin promoter), is made. This plasmid DNA plus plasmid DNA containing a PAT selectable marker is precipitated onto 1.1 μm (average diameter) tungsten pellets using a CaCl$_2$ precipitation procedure as follows:

100 μl prepared tungsten particles in water

10 μl (1 μg) DNA in TrisEDTA buffer (1 μg total)

100 μl 2.5 M CaCl$_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for root-preferred activity of the gene of interest, or for altered metal ion levels.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

EXAMPLE 3

Expression Data Using the promoter Sequences of the Invention

Nine μg of a transformation vector comprising the β-glucuronidase (GUS) operably linked to a promoter of the invention, plus 1 μg of a plasmid comprising the luciferase reporter gene operably linked to a ubiquitin promoter (Ubi::LUC) to act as a standard control is precipitated onto tungsten particles and bombarded onto maize embryos as described above. Shoots and roots are harvested separately and measured for GUS activity.

EXAMPLE 4

Transformation and Regeneration of Transgenic Plants using Agrobacterium Mediated Transformation For Agrobacterium-mediated transformation of maize with a nucleotide sequence of interest operably linked to a MT promoter of the invention, or with the MT coding sequences of the invention, preferably the method of Zhao is employed (U.S. Pat. No. 5,981,840), the contents of which are hereby incorporated by reference. In this method, immature embryos are isolated from maize and the embryos contacted with a suspension of Agrobacterium, where the bacteria are capable of transferring the gene of interest, or the MT coding sequences, to at least one cell of at least one of the immature embryos (step 1the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 5

Expression Analysis of the Metallothionein Promoter

Transient Expression Assays in Immature Maize Embryos:

The rmp5b genomic fragment containing the MT promoter and part of the 5' UTR was ligated into an expression vector containing β-glucuronidase (GUS) coding sequences. Such a vector is shown in FIG. 1, Plasmid M. The vector was constructed for Agrobacterium-mediated transformation as described in Example 4 above. The vector contained a Right border region(RB); an expression cassette comprising the MT promoter (MET PRO), the MT 5' UTR sequences (MT 5UTR), GUS exoni, the potato ST-LS1 intron 2, GUS exon 2, and the potato proteinase inhibitor termination region (PINII TERM) for GUS expression; an expression cassette comprising the CaMV35S promoter (CAMV35S PRO), PAT selection marker, and the CaMV35S termination region (CAMV35S TERM) for plant transformant selection; and a left border (LB).

Immature embryos were then transformed with plasmid M via Agrobacterium-mediated transformation as described in Example 4 above to generate stable maize transformants. A control plasmid, identical to plamid M except containing the constitutive ubiquitin promoter and enhancer region (ubiquitin exon 1 and part of ubiquitin intron 1) rather than the MT promoter and UTR, was used as a positive control. Staining of Immature Embryos for GUS activity:

GUS staining of GS3 immature embryos co-cultivating with Agrobacterium containing either the control plasmid or plasmid M consisted of placing embryos into the wells of a 48-well plate containing 0.5 ml of x-gluc solution (0.5 g x-gluc dissolved in 20 ml DMSO and 0.16 g $K_4Fe(CN)_6$ added separately to 1L of 0.1M $Na_2HPO_4$, pH7, 0.01M EDTA, 0.1% TritonX-100, 10% Methanol). Each plate contained immature embryos from either individual ears or a pool of 2–3 ears. The plates were sealed and incubated at 37° C. for 18 h after which the x-gluc solution was replaced with 0.5 ml of 70% ethanol. The results are summarized in Table I.

TABLE I

| Hours After Co-cultivation | Total No. of expressing GS3 embryos | |
|---|---|---|
| | Plasmid M | Control |
| 24 | 0 of 8 | 8 of 8 |
| 48 | 3 of 48 | 68 of 68 |
| 120 | 21 of 48 | 68 of 68 |

These results indicated that rmp5B genomic fragment comprising the metallothionein promoter was able to direct expression of the GUS coding region. Transgenic plants are regenerated to determine the strength, as well as root-specificity of the promoter.

EXAMPLE 6

Expression of the MT Gene in Maize

Expression of multiple genes (ESTs) in leaves (the $6^{th}$ leaf), stems (stalk), emerging crown roots (top nodal roots), adventitious roots, and corn rootworm (CRW)-eaten adventitious roots of V6 maize plants were compared, utilizing the GeneChip® microarray technology. See Lipshutz et al. (1999) *Nature Genetics Supplement* 21: 20–24; Li et al. (1999) *Developmental Biology* 211: 64–76. Briefly, using known methods, cDNA was synthesized from polyA+RNA isolated from the indicated tissues. Biotin-labeled cRNA was synthesized by in-vitro transcription of this cDNA using biotin-conjugated ribonucleotides. The cRNA was fragmented, hybridized to a customized GeneChip® array of *Zea mays*, washed, and stained with streptavidin (R-phycoerythrin conjugate) using the Affymetrix Inc.Gene-Chip Fluidics station.The Hewlett-Packard G2500A Gene Array Scanner and Affymetrix GeneChip Analysis software were used to analyze the results.

The developmental stage, V6, was selected because Western corn rootworm WCRW feed on maize roots between the stages of V4 and V8. Thus, a promoter active during these stages would be ideal to control the expression of a CRW insecticidal gene. V6 is defined by the maturation of the collar of the sixth leaf of the plant. CRW-eaten adventitious roots were generated by infesting each pot with 50 WCRW eggs. This resulted in roots that were damaged and scarred, but not decimated.

Analysis of the GeneChip results indicated the gene for EST CVRAQ62 (sequence set forth in SEQ ID NO:7), which belongs to the EST family corresponding to the nucleotide sequences for the expressed region of the maize MT gene (SEQ ID NO:2), was expressed in V6 adventitious roots at levels >250-fold higher than in V6 leaves. The same in V6 roots compared to V6 stalks. Comparing V6 adventitious roots to V6 crown roots showed only about a 2-fold greater level of expression in adventitious roots. A less than 2-fold difference was detected between adventitious roots and WCRW-eaten roots. These results indicate that the metallothionein gene of the present invention is highly expressed in root tissue, but not in leaf or stalk tissue. These data also indicate a high level of expression in emerging crown roots and in WCRW-eaten roots as there was not greater than a 3-fold difference in expression between adventitious roots, crown roots and WCRW-eaten roots. High expression in WCRW-eaten roots is significant because it indicates insect feeding does not down regulate the promoter.

Figure 2:
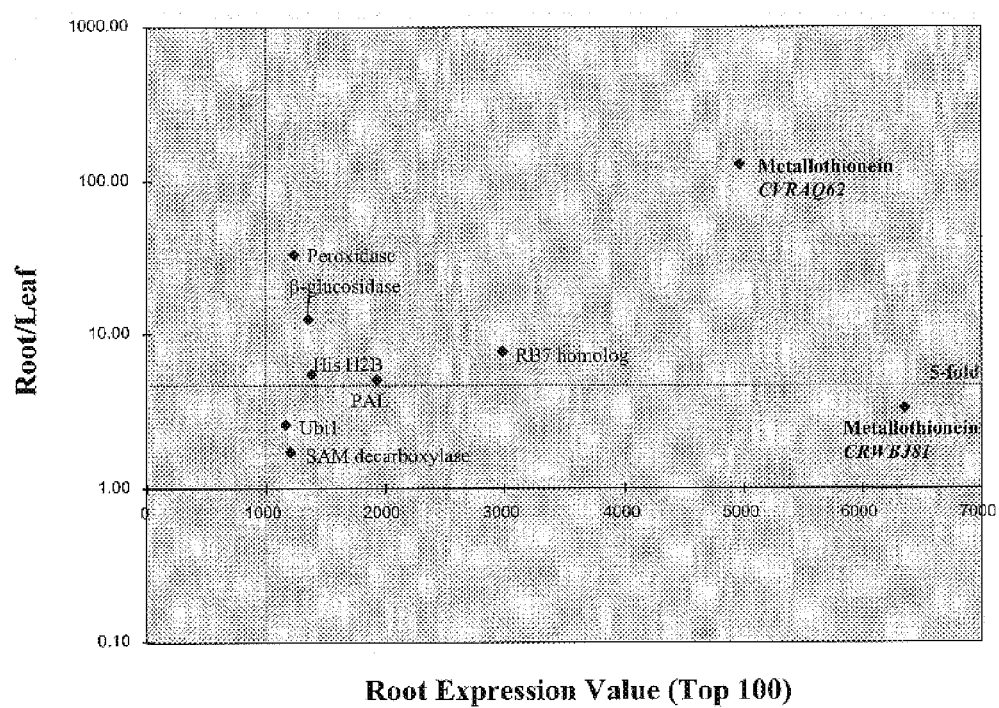
FIG. 2 depicts root-preferred expression of the MT gene of the invention, relative to other genes.

A second set of GeneChip microarray experiments were performed essentially as described above, and representative results are shown in FIG. 2. These results indicate high expression of the MT gene of the present invention represented by EST CRVAQ62, relative to a second maize MT gene represented by the EST CRWBJ81 (sequence set forth in SEQ ID NO:8) and other genes as shown in FIG. 2.

Figure 3:
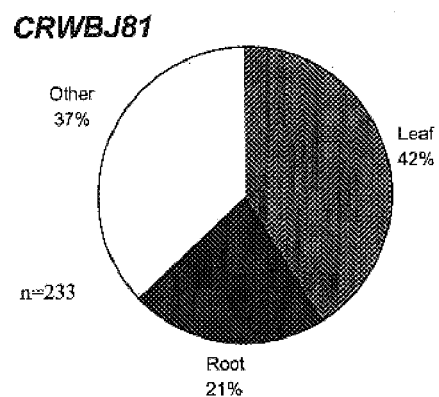
FIG. 3 depicts tissue distribution of expression of the MT gene of the invention relative to a second MT gene.
Figure 3:
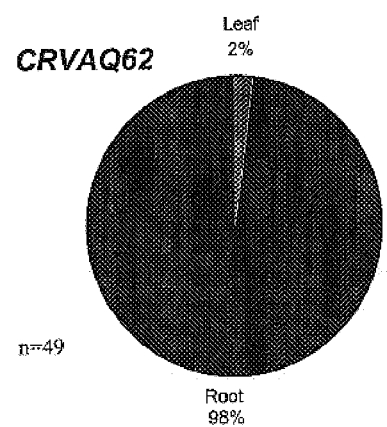

Northern blot experiments indicating root-preferred expression of the MT gene of the invention are not available. Electronic Northern blots showed tissue distribution of the MT gene of the present invention represented by EST CRVAQ62, relative to the second maize MT gene represented by the EST CRWBJ81; the results shown in FIG. 3.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid that is capable of driving transcription in a plant, wherein said nucleic acid comprises the nucleotide sequence set forth in SEQ ID NO:1.

2. A DNA construct comprising the nucleic acid of claim 1 and a nucleotide sequence operably linked to said nucleic acid.

3. A transformation vector comprising the DNA construct of claim 2.

4. A plant stably transformed with an expression cassette comprising a nucleic acid and a second nucleotide sequence operably linked to said nucleic acid, wherein said nucleic acid is capable of initiating transcription of said nucleotide sequence in a plant cell, wherein said nucleic acid comprises the nucleotide sequence set forth in SEQ ID NO:1.

5. The plant of claim 4, wherein said plant is a monocot.

6. The plant of claim 5 wherein said monocot is maize.

7. The plant of claim 4, wherein said plant is a dicot.

8. Transformed seed of the plant of claim 4, wherein said seed comprises said expression cassette in its genome.

9. A method for expressing a nucleotide sequence in a plant, said method comprising transforming a plant cell with a transformation vector comprising an expression cassette, and regenerating a stably transformed plant from said plant cell, said expression cassette comprising a nucleic acid and a second nucleotide sequence operably linked to said nucleic acid, wherein said nucleic acid is capable of initiating transcription of said second nucleotide sequence in a plant cell, and wherein said nucleic acid comprises the nucleotide sequence set forth in SEQ ID NO:1.

10. The method of claim 7, wherein expression of said operably linked second nucleotide sequence alters the phenotype of said plant.

11. A plant cell stably transformed with an expression cassette comprising a nucleic acid and a second nucleotide sequence operably linked to said nucleic acid, wherein said nucleic acid is capable of initiating transcription of said second nucleotide sequence in a plant cell, wherein said nucleic acid comprises the nucleotide sequence set forth in SEQ ID NO:1.

* * * * *

UNITED STATES PATENT AND TRADEMARK OFFICE
CERTIFICATE OF CORRECTION

PATENT NO. : 6,774,282 B1
DATED : August 10, 2004
INVENTOR(S) : Ritchie

It is certified that error appears in the above-identified patent and that said Letters Patent is hereby corrected as shown below:

Column 36,
Line 20, "claim 7" should read -- claim 9 --.

Signed and Sealed this

Twenty-eighth Day of September, 2004

JON W. DUDAS
*Director of the United States Patent and Trademark Office*

SEQUENCE LISTING

<160> NUMBER OF SEQ ID NOS: 18

<210> SEQ ID NO 1
<211> LENGTH: 747
<212> TYPE: DNA
<213> ORGANISM: Zea mays
<220> FEATURE:
<221> NAME/KEY: promoter
<222> LOCATION: (1)...(747)
<223> OTHER INFORMATION: Promoter sequence for maize metallothionein

<400> SEQUENCE: 1

```
cgacgggcat ttgcgtagtt gaagcttaca aagttgcata tgagatgagt gccggacatg      60
aagcggataa cgttttaaac tggcaacaat atctagctgt ttcaaattca ggcgtgggaa     120
gctacgccta cgcgccctgg acggcgtgta aagagccagc atcggcatca ttgtcaaacg     180
atcgacaagg ccaagaaatt ccaaatatat tattaataaa aagaaggca caaattagtt     240
tggtttttta gtatgtgtgg cggaggaaat tttgagaacg aacgtatcaa agaaggcaca     300
agacgatata gattgacgcg gctagaagtt gcagcaagac agtgggtacg gtcttatata     360
tcctaataaa taaaaaataa aactatagtg tgtcaaatgt caacaagagg aggaggcagc     420
caaattagca gagggagaca agtagagcac gccttattag cttgcttatt tatcgtggtg     480
gtgtacttgt taattactgg cacgcattat caacaacgca gttctggatg tgaatctaga     540
caaacatttg tctaggttcc gcacgtatag ttttttttcct ctttttttg gggggggggt     600
gggggggga acggaagctg taataaacgg tactaggaac gaaagcaacc gccgcgcgca     660
tgttttttgca atagattacg gtgaccttga tgcaccaccg cgtgctataa aaaccagtgt     720
ccccgagtct actcatcaac caatcca                                         747
```

<210> SEQ ID NO 2
<211> LENGTH: 612
<212> TYPE: DNA
<213> ORGANISM: Zea mays
<220> FEATURE:
<221> NAME/KEY: CDS
<222> LOCATION: (69)...(308)
<223> OTHER INFORMATION: Coding sequence for maize metallothionein

<400> SEQUENCE: 2

```
taactcgaaa cctttctctg tgctctgttc tgtctgtgtg tttccaaagc aaacgaaaga      60 ggtcgagg atg tct tgc agc tgc gga tca agc tgc aac tgc gga tca agc     110
         Met Ser Cys Ser Cys Gly Ser Ser Cys Asn Cys Gly Ser Ser
         1               5                  10 tgc aag tgc ggc aag atg tac cct gac ctg gag gag aag agc ggc ggg     158
Cys Lys Cys Gly Lys Met Tyr Pro Asp Leu Glu Glu Lys Ser Gly Gly
 15                  20                  25                  30 ggc gct cag gcc agc gcc gcc gcc gtc gtc ctc ggc gtt gcc cct gag     206
Gly Ala Gln Ala Ser Ala Ala Ala Val Val Leu Gly Val Ala Pro Glu
                 35                  40                  45 acg aag aag gcg gcg cag ttc gag gcg gcg ggc gag tcc ggc gag gcc     254
Thr Lys Lys Ala Ala Gln Phe Glu Ala Ala Gly Glu Ser Gly Glu Ala
             50                  55                  60 gct cac ggc tgc agc tgc ggt gac agc tgc aag tgc agc ccc tgc aac     302
Ala His Gly Cys Ser Cys Gly Asp Ser Cys Lys Cys Ser Pro Cys Asn
         65                  70                  75 tgc tga tcctgctgcg ttgtttcgtt tgcggcatgc atggatgtca ccttttttttt      358
Cys *
```

```
actgtctgct ttgtgcttgt ggcgtgtcaa gaataaagga tggagccatc gtctggtctg      418
actctggctc tccgccatgc atgcttggtg tcggttctgt tgtgcttgtg ttggtgcatg      478
taatcgtatg gcatcgttac acaccatgca tctctgatct ctttgcgcca gtgtgtgtga      538
ctatgtccct gtaacgattg gctcagtgat tgaatatata tacaatactg ttttactaaa      598
aaaaaaaaaa aaaa                                                        612
```

```
<210> SEQ ID NO 3
<211> LENGTH: 79
<212> TYPE: PRT
<213> ORGANISM: Zea mays

<400> SEQUENCE: 3
```

```
Met Ser Cys Ser Cys Gly Ser Ser Cys Asn Cys Gly Ser Ser Cys Lys
 1               5                  10                  15

Cys Gly Lys Met Tyr Pro Asp Leu Glu Glu Lys Ser Gly Gly Gly Ala
            20                  25                  30

Gln Ala Ser Ala Ala Ala Val Val Leu Gly Val Ala Pro Glu Thr Lys
        35                  40                  45

Lys Ala Ala Gln Phe Glu Ala Ala Gly Glu Ser Gly Glu Ala Ala His
    50                  55                  60

Gly Cys Ser Cys Gly Asp Ser Cys Lys Cys Ser Pro Cys Asn Cys
65                  70                  75
```

```
<210> SEQ ID NO 4
<211> LENGTH: 26
<212> TYPE: DNA
<213> ORGANISM: Artificial Sequence
<220> FEATURE:
<223> OTHER INFORMATION: Gene specific synthetic primer for MT promoter
      isolation

<400> SEQUENCE: 4
atcttgccgc acttgcagct tgatcc                                            26
```

```
<210> SEQ ID NO 5
<211> LENGTH: 24
<212> TYPE: DNA
<213> ORGANISM: Artificial Sequence
<220> FEATURE:
<223> OTHER INFORMATION: Gene specific primer for MT promoter isolation

<400> SEQUENCE: 5
cagttgcagc ttgatccgca gctg                                              24
```

```
<210> SEQ ID NO 6
<211> LENGTH: 21
<212> TYPE: DNA
<213> ORGANISM: Artificial Sequence
<220> FEATURE:
<223> OTHER INFORMATION: Gene specific primer for MT promoter isolation

<400> SEQUENCE: 6
caggatcctc gacctctttc g                                                 21
```

```
<210> SEQ ID NO 7
<211> LENGTH: 255
<212> TYPE: DNA
<213> ORGANISM: Zea mays

<400> SEQUENCE: 7
cttgcaactg cggatcaagc tgcggctgcg gctcaagctg caagtgcggc aagaagtacc       60
```

-continued

```
ctgacctgga ggagacgagc accgccgcgc aggccaccgt cgtcctcggc gtggccccgg      120
agaagaaggc cgcgcccgag ttcgtcgagg ccgcggcgga gtccggcgag gccgcccacg      180
gctgcagctg cggtggcaac tgcaagtgcg accoctgcaa ctgctgatca catcgatcga      240
cgaccatgga tatga                                                      255
```

<210> SEQ ID NO 8
<211> LENGTH: 255
<212> TYPE: DNA
<213> ORGANISM: Zea mays

<400> SEQUENCE: 8

```
gtgctctgtt ctgtctgtgt gtttccaaag caaacgaaag aggtcgagga tgtcttgcag       60
ctgcggatca agctgcaact gcggatcaag ctgcaagtgc ggcaagatgt accctgacct      120
ggaggagaag agcggcgggg cgctcaggc cagcgccgcc gccgtcgtcc tcggcgttgc      180
ccctgagacg aagaaggcgg cgcagttcga ggcggcgggc gagtccggcg aggccgctca      240
cggctgcagc tgcgg                                                      255
```

<210> SEQ ID NO 9
<211> LENGTH: 15
<212> TYPE: DNA
<213> ORGANISM: Zea mays
<220> FEATURE:
<221> NAME/KEY: misc_feature
<222> LOCATION: (1)...(15)
<223> OTHER INFORMATION: Maize promoter element

<400> SEQUENCE: 9

```
aaattagcag aggga                                                       15
```

<210> SEQ ID NO 10
<211> LENGTH: 10
<212> TYPE: DNA
<213> ORGANISM: Zea mays
<220> FEATURE:
<221> NAME/KEY: misc_feature
<222> LOCATION: (1)...(10)
<223> OTHER INFORMATION: Maize promoter element

<400> SEQUENCE: 10

```
tatgagatga                                                             10
```

<210> SEQ ID NO 11
<211> LENGTH: 10
<212> TYPE: DNA
<213> ORGANISM: Zea mays
<220> FEATURE:
<221> NAME/KEY: misc_feature
<222> LOCATION: (1)...(10)
<223> OTHER INFORMATION: Maize promoter element

<400> SEQUENCE: 11

```
cgatcgacaa                                                             10
```

<210> SEQ ID NO 12
<211> LENGTH: 9
<212> TYPE: DNA
<213> ORGANISM: Zea mays
<220> FEATURE:
<221> NAME/KEY: misc_feature
<222> LOCATION: (1)...(9)
<223> OTHER INFORMATION: Maize promoter element -continued

```
<400> SEQUENCE: 12 ggcacaaga                                                              9

<210> SEQ ID NO 13
<211> LENGTH: 9
<212> TYPE: DNA
<213> ORGANISM: Zea mays
<220> FEATURE:
<221> NAME/KEY: misc_feature
<222> LOCATION: (1)...(9)
<223> OTHER INFORMATION: Maize promoter element

<400> SEQUENCE: 13 gatatagat                                                              9

<210> SEQ ID NO 14
<211> LENGTH: 9
<212> TYPE: DNA
<213> ORGANISM: Zea mays
<220> FEATURE:
<221> NAME/KEY: misc_feature
<222> LOCATION: (1)...(9)
<223> OTHER INFORMATION: Maize promoter element

<400> SEQUENCE: 14 agagcacgc                                                              9

<210> SEQ ID NO 15
<211> LENGTH: 7
<212> TYPE: DNA
<213> ORGANISM: Zea mays
<220> FEATURE:
<221> NAME/KEY: misc_feature
<222> LOCATION: (1)...(7)
<223> OTHER INFORMATION: Maize promoter element

<400> SEQUENCE: 15 agttctg                                                                7

<210> SEQ ID NO 16
<211> LENGTH: 7
<212> TYPE: DNA
<213> ORGANISM: Zea mays
<220> FEATURE:
<221> NAME/KEY: misc_feature
<222> LOCATION: (1)...(7)
<223> OTHER INFORMATION: Maize promoter element

<400> SEQUENCE: 16 agctgta                                                                7

<210> SEQ ID NO 17
<211> LENGTH: 9
<212> TYPE: DNA
<213> ORGANISM: Zea mays
<220> FEATURE:
<221> NAME/KEY: misc_feature
<222> LOCATION: (1)...(9)
<223> OTHER INFORMATION: Maize promoter element

<400> SEQUENCE: 17 atagattac                                                              9

<210> SEQ ID NO 18
<211> LENGTH: 19
<212> TYPE: DNA
<213> ORGANISM: Artificial Sequence
```

```
<220> FEATURE:
<223> OTHER INFORMATION: Oligonucleotide primer

<400> SEQUENCE: 18
actatagggc acgcgtggt                                                    19
```